United States Patent [19]

Frome

[11] Patent Number: 5,260,313
[45] Date of Patent: Nov. 9, 1993

US005260313A

[54] DIAGNOSIS AND TREATMENT OF VARIOUS NEURALGIAS

[75] Inventor: Bruce Frome, Bel Air, Calif.

[73] Assignee: National Pain Institute, Inc., Marina Del Rey, Calif.

[21] Appl. No.: 849,770

[22] Filed: Mar. 12, 1992

[51] Int. Cl.$^5$ .......................... A61K 31/23; C12Q 1/00
[52] U.S. Cl. .................................. 514/552; 514/817; 514/934; 435/4
[58] Field of Search ..................... 424/195.1; 514/552, 514/817, 934; 435/4

[56] References Cited

U.S. PATENT DOCUMENTS

| | | | |
|---|---|---|---|
| 4,311,617 | 1/1982 | Ansari | 252/522 R |
| 4,599,677 | 7/1986 | Lawless | 361/321 |
| 4,923,685 | 5/1990 | Wuelkhitz | 424/54 |
| 4,940,583 | 7/1990 | Thompson | 424/195.1 |

*Primary Examiner*—John W. Rollins
*Attorney, Agent, or Firm*—Lyon & Lyon

[57] ABSTRACT

The present invention relates to a method of diagnosing and treating neuropathic pain syndromes with a composition of which *Pelaroonium graveolens* Ait. oil is the principle therapeutic agent. This oil is alternatively called geranium oil bourbon, oil geranium reunion, and oil rose-geranium. In particular, this invention discloses a method and composition to be used in treating and diagnosing neuropathic pain syndromes, including but not limited to Postherpetic Neuralgia and Reflex Syndrome Dystrophy, in which geranium oil bourbon is applied topically to the area affected with neuropathic pain symptoms.

This invention provides a previously unavailable method for distinguishing pain caused by Postherpetic Neuralgia or by Reflex Syndrome Dystrophy from that caused by a host of other neuropathies. Additionally, this invention provides a previously unavailable means of treating the often unbearable pain caused by these two neuropathies.

12 Claims, No Drawings

5,260,313

DIAGNOSIS AND TREATMENT OF VARIOUS NEURALGIAS

FIELD OF THE INVENTION

This invention relates to the diagnosis and treatment of various specific neuralgias through the administration of compounds described and claimed herein which are capable of greatly reducing or eliminating the pain associated with these neuralgias.

BACKGROUND OF THE INVENTION

Neuropathic pain encompasses various pain syndromes associated with disorders of the peripheral and central nervous system. Despite hypothetical pathophysiologic mechanisms for neuropathic pain, the true underlying pathophysiology of these pains remains elusive. This is especially true when the neuropathic pain syndromes exhibit a diverse array of symptoms and unusual sensations such as burning, shooting, aching or electrifying pain, feelings of bodily distortion, allodynia and hyperpathia. Not only are curative measures for the neural abnormalities unavailable but symptomatic treatments are often ineffective causing an enormous problem for clinicians in treatment and management of neuropathic pain. In addition, since a large number of patients experiencing neuropathic pain remain intractable to standard therapies, it is hard for a clinician to match a particular treatment within a particular patient. This causes particular problems with diagnosis of the neuropathic pain syndromes.

1. Neuropathic Pain Management

Of the various neuropathic pain syndromes, two groups, Neuralgias and Reflex Sympathetic Dystrophies, remain a common problem to clinicians as to treatment and pain management. Neuralgia is the paroxysmal pain extending along the course of one or more nerves. Although numerous neuralgias exist, Postherpetic Neuralgia ("PHN") is one of the most incapacitating neuralgias. PHN is a major chronic complication of Herpes Zoster. Herpes Zoster results from reactivation of latent *Varicella zoster* viral infection (chicken pox) and is most common in elderly patients and immunosuppressed patients. The persistent and excruciating pain resulting from PHN often leads to profound depression and is the number one cause of suicide from pain afflictions.

The pain from PHN persists long after the rash of Herpes Zoster has subsided and healed. It is rarely found with people under 40 years of age and is seen in 50% of patients over the age of 60. The pain, which is limited to affected dermatomes, is described as very severe and sharp in character with sometimes burning sensations. Although it is virtually always present to some extent, it may suddenly and without warning intensify over any dermatome, resulting in agonizing paroxysms of pain.

Unfortunately the cause of PHN remains obscure. Specific remedies are unavailable and symptomatic ones are often ineffective. Often the pain is associated with hyperesthesia in which any stimulus, even contact with clothing, is unbearable. Simple tasks, such as bathing, may become impossible. Not surprisingly, sleep is often disturbed. Any movement may intensify the pain.

A large number of drugs have been used in an effort to prevent PHN. These include corticosteroids, amantadine, levodopa, vidarabine, alpha interferon and acyclovir. The effect of those preventive treatments have been unclear. Treatment and pain management, however, have been more effective. Although a wide variety of therapies have been used providing significant benefits for patients with PHN, no one treatment is uniformly successful. The skillful use of analgesic, anti-inflammatory, and psychotropic drugs can provide substantial relief. The best treatments currently available for PHN are amitriptyline, transcutaneous electrical stimulation, and topical Capsaicin.

Capsaicin is a naturally occurring compound found in the fruit of several members of the various species of Capsaicin or Solanaceae (pepper plants). Topically applied, capsaicin is thought to act by depleting substance P, the primary chemomediator of painful impulses from the periphery to the central nervous system, from cell bodies and nerve terminals. Other types of topical applications used to relieve PHN pain include use of benzydamine, lignocaine, prilocaine, lidocaine or vitamin E. Transcutaneous Electrical Stimulation (TES) is believed to reduce pain by activating large low-threshold nerve fibers, counteracting the increased discharges from small unmyelinated fibers. Amitriptyline, a tricyclic antidepressant, is effective in relieving PHN independently of relieving the depression associated with neuropathic pain syndromes. The tricyclic antidepressants are believed to function as analgesics through their ability to block re-uptake of serotonin and norepinephrine.

Another group of neuropathic pain syndromes in which pain management is a problem are Reflex Sympathetic Dystrophies ("RSD"). RSD is an all inclusive term applied to a great variety of neuropathic pain syndromes associated with autonomic dysfunction occurring after injury. These include minor causalgia, posttraumatic pain syndrome, posttraumatic painful arthrosis, Sudeck's atrophy, sympathalgia, shoulder-hand syndrome and chronic traumatic edema.

In general, RSD is an intensely unpleasant burning pain felt in a limb where there has been partial damage to the sympathetic and somatic sensory nerves. RSD may occur as the aftermath of various forms of mild tissue injury, ranging from direct trauma to less obvious injuries like infection or radiation therapy. It is characterized by pain and tenderness of an extremity, swelling of soft tissues, trophic changes in the involved extremity (skin atrophy, pigmentation changes, hypertrichosis, hyperhidrosis, nail changes), vasomotor instability, patchy osteoporosis, limitation of motion, hyper-sensitivity to cold, stiffness and paresthesia. The etiology, however, is still debated.

Several modes of treatment for RSD have been suggested, depending on the severity. If RSD is diagnosed early in the course when symptoms are mild, standard therapies include warm whirlpool baths, heat, massage, active and passive exercise. If pain becomes too severe analgesics and sedatives are used. Successful treatment has also been documented with transcutaneous electrical stimulations, regional sympathetic ganglion blocks utilizing local anesthetics or as a last resort surgical sympathectomy.

2. Diagnosis of Neuropathic Pain Syndromes

Another major issue regarding neuropathic pain syndromes is the ability to diagnose these syndromes. Since neuropathic pain encompasses a large variety of pain syndromes with varying pain symptoms which respond differently to various standard therapies, it is difficult to diagnose patients into heterogeneous groups of neuropathic pain. The current diagnostic categories tend to lump patients together with a variety of underlying physiological mechanisms of pain with distinct patterns of response to various drugs. Thus it is hard for clinicians to match a particular patient with a particular treatment. Diagnostic classifications are needed such that more defined individualized treatment can occur.

3. Geranium Oil

Geranium oil has been used extensively in perfumery, as an insect repellent, and for other related purposes. For example, U.S. Pat. No. 4,940,583 to Thompson, describes the use of geranium oil as a component in an animal repellent composition. U.S. Pat. No. 4,923,685 to Forg et al. describes the use of geranium oil as part of a mouth wash composition. U.S. Pat. No. 4,579,677 to Hooper et al. describes the use of geranium oil as a scenting agent in a bleaching composition. U.S. Pat. No. 4,311,617 to Ansari et al. describes the use of geranium oil in perfumery compositions.

The geranium oil is derived from plants of the genus Pelarconium of the family Geraniaceae. The primary constituents of most geranium oils are geraniol (trans-3,7-dimethyl-2,6-octadien-1-ol) and citronellol (3,7-dimethyl-6-octen-1-ol). Minor constituents include geranial (3,7-dimethyl-2,6-octadienol), citronellal (3,7-dimethyl-6-octenal), linalool (2,6-dimethyl-2,7-octadiene-6-ol), pelargonic acid (nonanoic acid and rhodinol (3,7-dimethyl-7-octen-1-ol).

A variety of species of geranium plants exist throughout the world, with most having approximately the same chemical constituents in the extracted oil. However, one species which grows almost uniquely in the Reunion Islands, *Pelargonium graveolens*, Ait., has a unique chemical composition.

The present invention relates to the above described two common but crucial problems with Neuropathic Pain Syndromes: pain management and diagnosis. It addresses both the current difficulty in diagnosing the type of neuropathy present, as well as the difficulty in prescribing a treatment which will be effective for a particular patient. It describes the use of a particular geranium oil in solving these problems.

SUMMARY OF THE INVENTION

The present invention relates to a method of diagnosing and treating neuropathic pain syndromes with a composition of which *Pelargonium graveolens* Ait. oil is the principle therapeutic agent. This oil is alternatively called geranium oil bourbon, oil geranium reunion, and oil rose-geranium, and will be referred to hereafter as geranium oil bourbon. In particular, this invention discloses a method and composition to be used in treating and diagnosing neuropathic pain syndromes, including but not limited to Postherpetic Neuralgia and Reflex Syndrome Dystrophy, in which geranium oil bourbon is applied topically to the area affected with neuropathic pain symptoms.

This invention provides a previously unavailable method for distinguishing pain caused by Postherpetic Neuralgia or by Reflex Syndrome Dystrophy from that caused by a host of other neuropathies. Additionally, this invention provides a previously unavailable means of treating the often unbearable pain caused by these two neuropathies.

DESCRIPTION OF THE INVENTION

1. Source

In the practice of the present invention, an oil from a specific species of geraniums has been discovered which when topically applied to an area affected with pain, is diagnostic for, as well as effective in treating, particular neuropathic pain syndromes. The geranium oil bourbon used as the active ingredient of this preparation for neuropathic pain is prepared from the geranium species *Pelargonium graveolans* Ait. This species of geranium plant grows specifically in the Reunion Islands, as well as in other locales. Oil extracted from other species of geranium plants is ineffective in either diagnosis or treatment of neuropathies.

The oil is prepared from *Pelargonium graveolans* Ait. geraniums according to known techniques in the art. For example, the oil can be extracted by steam distillation of fresh plants, harvested at the period of initial bloom. The oil is commercially readily available, such as from Tiferet International.

The oil can be distributed in a pharmaceutically acceptable carrier. The geranium oil bourbon can be applied using techniques known in the art in various pharmaceutically acceptable carriers such as emulsions, solutions or suspensions including lotions, creams or ointments. These carriers can contain volatile diluents, such as alcohol (e.g. isopropyl alcohol) or glycol, as well as wetting, emulsifying and suspending agents.

2. Application

The geranium oil bourbon, used alone or in a composition with a pharmaceutically acceptable carrier, is topically applied in therapeutically effective amounts to areas of the human body affected with symptoms of neuropathic pain syndromes. Dosage amounts depend on the patient's affected areas. Normally 1-10 drops are used, 1 drop for smaller affected area and 10 drops with larger affected areas or areas exhibiting excruciating pain symptoms. The oil or composition containing the oil is applied to the complete area affected with pain and left to be absorbed by the skin.

The initial treatment of an area of the human body exhibiting neuropathic pain produces a numbness similar to a topical anesthetic applied to the skin which reduces or absorbs sensation. An initial burning reaction occurs upon application but quickly subsides. However, application of the oil to the affected area using the bare fingers does not provide the numbing or burning sensation to the fingers.

Once administered, significant reduction in pain and reduction in swelling occurs. The superficial pain, which is the most excruciating, decreases in minutes. The deeper pain, which is less severe, decreases shortly thereafter. In all patients tested, an 80-100% reduction in neuropathic pain resulted from application of the geranium oil bourbon to the affected area. The pain remains diminished or absent for a period of time ranging from 2-24 hours. Additional dosages of the geranium oil bourbon or composition can be applied as needed as the pain returns.

3. Diagnosis

Because of the effectiveness of the geranium oil bourbon in treating particular neuropathies, the use of this oil is also diagnostic for those neuropathies. This is beneficial as it provides the opportunity not only to treat the symptoms using geranium oil, but also potentially to prevent or treat the cause of the pain. Additionally accurate diagnosis of the neuropathy allows the medical practitioner to terminate treatments which are specific for different diseases but which were being used in an effort to relieve pain. Likewise, a diagnosis that rules out certain neuropathies due to the patient's lack of response to the geranium oil bourbon will allow the medical practitioner to pursue other treatments.

Geranium oil bourbon is specifically diagnostic for both PHN and RSD. These two types of neuropathies can then be distinguished by other characteristics which have previously been found to be associated with one or the other. For example, a patient with PHD would have a history of infection by *Varicella zoster* virus, often resulting in chicken pox, and a recent rash at or near the site of the neuralgia.

Diagnosis is performed by applying the geranium oil bourbon as described above for treatment and observing the presence or absence of relief from pain. The reaction is relatively quick (within around 5 minutes of application), and easily distinguishable. From 80-100% of a patient's pain is relieved if the causative neuropathy is PHN or RSD, while very little or no relief is provided for other neuropathies.

The following example further illustrates the present invention. It will be apparent to those skilled in the art that only the preferred embodiment has been described in the following example and that there are various modifications and alterations which fall within the scope of this invention and are intended to be covered by the claims appended hereto.

EXAMPLE 1

The geranium oil bourbon was applied directly to the skin of 200 patients exhibiting neuropathic pain. These patients exhibited symptoms from either Reflex Sympathetic Dystrophy or Postherpetic Neuralgia Syndromes. These symptoms included burning and lancelating pain, and redness and swelling of the skin. The oil was applied by rubbing it lightly over the skin area affected by pain. Approximately, 1-10 oil drops were used per area, depending on the size of the affected tissue and intensity of the pain. The oil was left to be absorbed into the skin.

Within approximately three (3) minutes patients developed partial pain relief. The patients experienced an initial burning and numbness at the affected area before reduction in pain developed. Patients' superficial pain was substantially gone within five (5) to seven (7) minutes. The deeper, but duller, pain subsided within approximately 20 minutes. In all patients studied there was an 80-100% reduction in pain. This reduction of pain lasted from two (2) to twenty-four (24) hours.

I claim:

1. A method of treating Postherpetic Neuralgia or Reflex Sympathetic Dystrophy pain in patients comprising topically applying a therapeutically effective amount of geranium oil bourbon to skin areas affected with said pain.

2. The method of claim 1 wherein the geranium oil bourbon is present in a pharmaceutically acceptable carrier.

3. The method of claim 1 wherein the geranium oil bourbon is applied at least daily.

4. The method of claim 3 wherein the geranium oil bourbon is applied more than once daily.

5. The method of claim 1 wherein the geranium oil bourbon is left on the skin to be absorbed into the skin of the affected area.

6. The method of claim 1 wherein the geranium oil bourbon is repeatedly applied.

7. A method of diagnosing Postherpetic Neuralgia or Reflex Sympathetic Dystrophy pain in patients comprising topically applying a diagnostically effective amount of geranium oil bourbon to skin areas affected with said pain, and observing a significant decrease in said pain.

8. The method of claim 7 wherein the geranium oil bourbon is present in a pharmaceutically acceptable carrier.

9. The method of claim 7 wherein the geranium oil bourbon is applied topically.

10. The method of claim 7 wherein the geranium oil bourbon is left on the skin to be absorbed into the skin of the affected area.

11. The method of claim 7 wherein the reduction of pain is further associated with a reduction in redness of the affected skin area.

12. The method of claim 7 wherein the reduction of pain is further associated with a reduction in swelling of the affected skin area.

* * * * *